US00PP18946P2

(12) United States Plant Patent
Emmons

(10) Patent No.: US PP18,946 P2
(45) Date of Patent: Jun. 17, 2008

(54) APPLE TREE, 'EMMONS'

(50) Latin Name: *Malus Pumila Mil*
Varietal Denomination: Emmons

(75) Inventor: Donald C. Emmons, Yakima, WA (US)

(73) Assignee: Zirkle Fruit Company, Selah, WA (US)

( * ) Notice: Subject to any disclaimer, the term of this patent is extended or adjusted under 35 U.S.C. 154(b) by 0 days.

(21) Appl. No.: 11/639,449

(22) Filed: Dec. 15, 2006

(51) Int. Cl.
*A01H 5/00* (2006.01)

(52) U.S. Cl. ..... Plt./161

(58) Field of Classification Search ..... Plt./121
See application file for complete search history.

*Primary Examiner*—Annette H Para
(74) *Attorney, Agent, or Firm*—Wells St. John P.S.

(57) ABSTRACT

A new and distinct variety of apple tree 'Malus Pumila Mil' named 'Emmons' and which is characterized as to novelty by a uniqueness of shape, color, flavor and texture of the fruit, and a date of maturity for commercial harvesting and shipment of about September 29$^{th}$ under the ecological conditions prevailing in Central Washington.

4 Drawing Sheets

BACKGROUND OF THE NEW VARIETY

The present invention relates to a new and distinct variety of apple tree 'Malus Pumila Mil' and which has been denominated varietally as 'Emmons' and more particularly to an apple tree which bears a distinctively colored round apple which has a dense sweet flesh, and which further is noteworthy because it retains its firmness after harvesting and can be stored for long periods of time with little deterioration in the overall quality of the fruit.

ORIGIN AND ASEXUAL REPRODUCTION

It has long been recognized that a very important factor contributing to the success of any variety of apple tree bearing fruit for the fresh market is its ability to produce an attractively colored fruit, which has a distinctive noteworthy flavor, and which further has good handling and storage characteristics. The new variety 'Emmons' is noteworthy as noted above, in producing an attractively and distinctively colored fruit having a distinctive pink stripe over a cream-yellow background and which further has a distinctive taste, dense flesh and a sweetness with a hint of tartness. The new variety is firm at harvest and can be handled with little skin or flesh damage. The new variety 'Emmons' is harvested during the same season where other well-known varieties such as the Red Delicious (unpatented) are harvested under the ecological conditions prevailing in the Columbia Basin of Washington State. However, the present variety is noteworthy in producing a highly desirable dessert-type apple having noteworthy characteristics which distinguish it from other varieties which it is mostly similar to.

The new variety of apple tree 'Malus Pumila Mil' was discovered as a chance seedling growing within the cultivated area of the Applicant's orchard which is located near Gleed, Wash. The inventor discovered the chance seedling following the purchase of the same orchard in 1978. The orchard contained a variety of different apple trees including Golden Delicious (unpatented), and several different cultivars of Red Delicious apple trees all of which are unpatented. The inventor, with the intent that he would remove and replant trees in the future, deferred maintenance for several years allowing the chance seedling to develop. Subsequently, the inventor noted the chance seedlings unique characteristics and marked the variety for subsequent observation. In 1993, the inventor removed wood from the original tree and bench grafted it onto 'M-7' rootstock (unpatented). This original asexual reproduction in Gleed, Wash., produced 20 trees which were then planted in a nearby orchard. These test trees have since produced fruit and the inventor has confirmed that this first asexual propagation resulted in apple trees being produced which possess the same distinctive characteristics as the original chance seedling. Additional asexual reproductions have taken place in the years 1997–2004. These subsequent asexual reproductions have also confirmed the unique characteristics of the new apple tree.

The present variety 'Emmons' is most similar in its date of harvesting to the Red Delicious apple tree named 'Bisbee' (U.S. Plant Pat. No. 1,565) when grown under the same ecological conditions. In relative comparison to the 'Bisbee' apple tree, the 'Emmons' apple tree produces fruit which is round in relative comparison to the elongated Red Delicious apple shape that is quite familar to those who are skilled in the art. Still further, the 'Emmons' apple tree produces a fruit which has a pink stripe over a cream-yellow background that is unlike the coloration of any Red Delicious variety which is known. Still further, the growing characteristics of typical Red Delicious apple trees, especially the 'Bisbee' cultivar is typically more upright, then spreading, and its growth is only moderately vigorous. In relative comparison, the 'Emmons' apple tree is more spreading in form than most Red Delicious cultivars, and this growth pattern appears more vigorous. Still further, the 'Emmons' apple tree produces a fruit that has a unique and pleasing taste which is distinctly different from the fruit produced by known Red Delicious cultivars.

SUMMARY OF THE VARIETY

The 'Emmons' apple tree is characterized principally by novelty by producing a unique, attractively colored round-shaped apple which is ripe for harvesting and shipment about September 29$^{th}$ under the conditions prevailing in the Columbia Basin of central Washington State.

BRIEF DESCRIPTION OF THE DRAWINGS

The accompanying drawings are color photographs of the present variety. These photographs depict whole fruit, fruit dissected in both the axial plane, as well as the plane transverse to the axial plane, typical leaves of the variety, and the branching habit of the same variety. Still further, a photograph is provided showing the present variety of fruit along side the fruit produced by the variety which is most closely similar to the date of harvesting of this new variety. The external coloration of the fruit as shown in these photographs is sufficiently matured for harvesting and shipment. These colors are as nearly true as reasonably possible and a color representation of this type. Due to chemical development, processing and printing, the leaves and fruit depicted in these photographs may or may not be accurate when compared to the actual specimen. For this reason, future color references should be made to the color plates (Royal Horticulture Society), and descriptions provided hereinafter. Occasionally, common color names will also be used.

DETAILED DESCRIPTION

Figure 1:
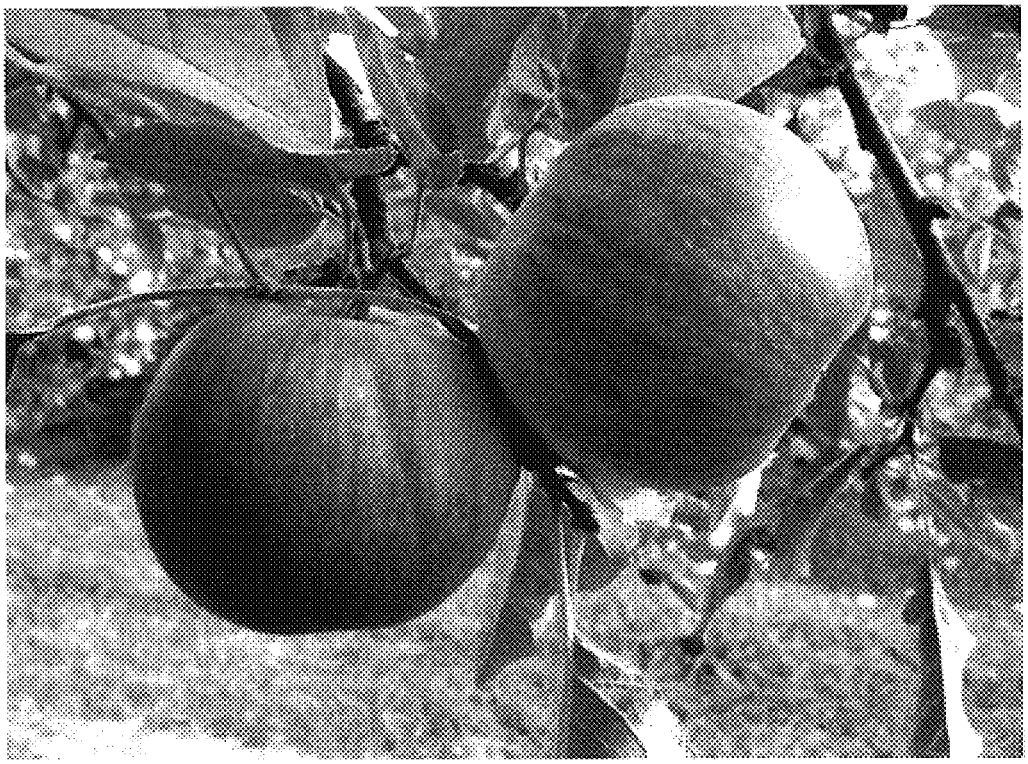
FIG. 1 shows the fruiting habit of the present variety. The apples as seen in this photograph are sufficiently matured for harvesting and shipment.
Figure 2:
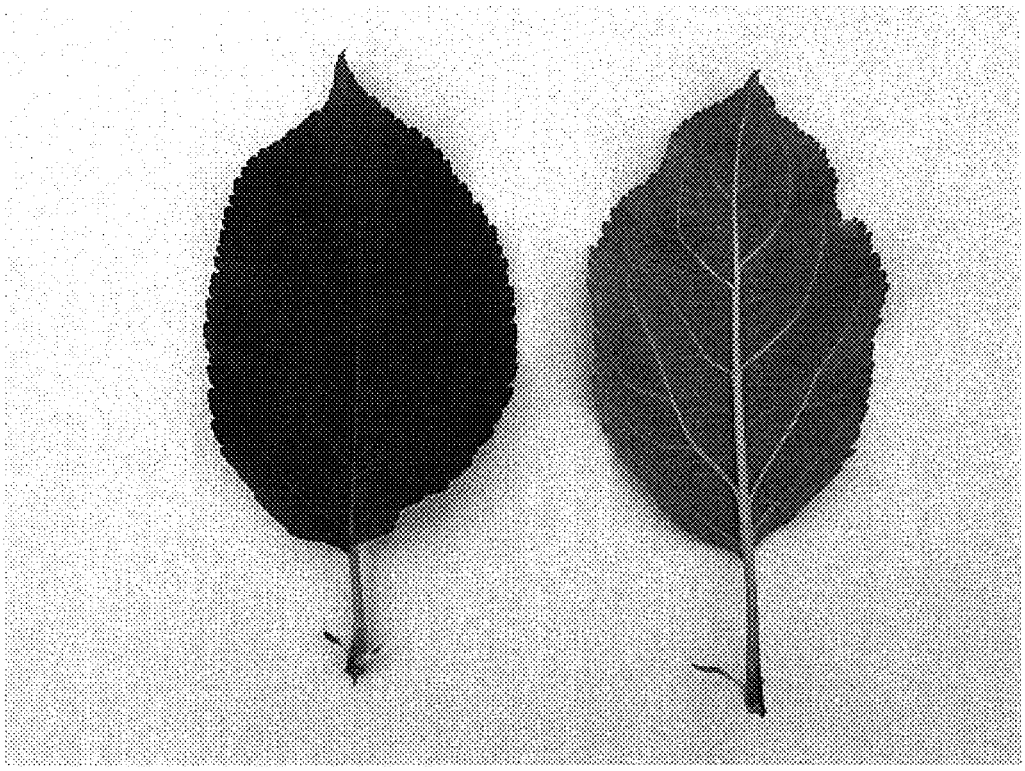
FIG. 2 shows both the dorsal and ventral coloration of typical leaves taken from the present variety.
Figure 3:
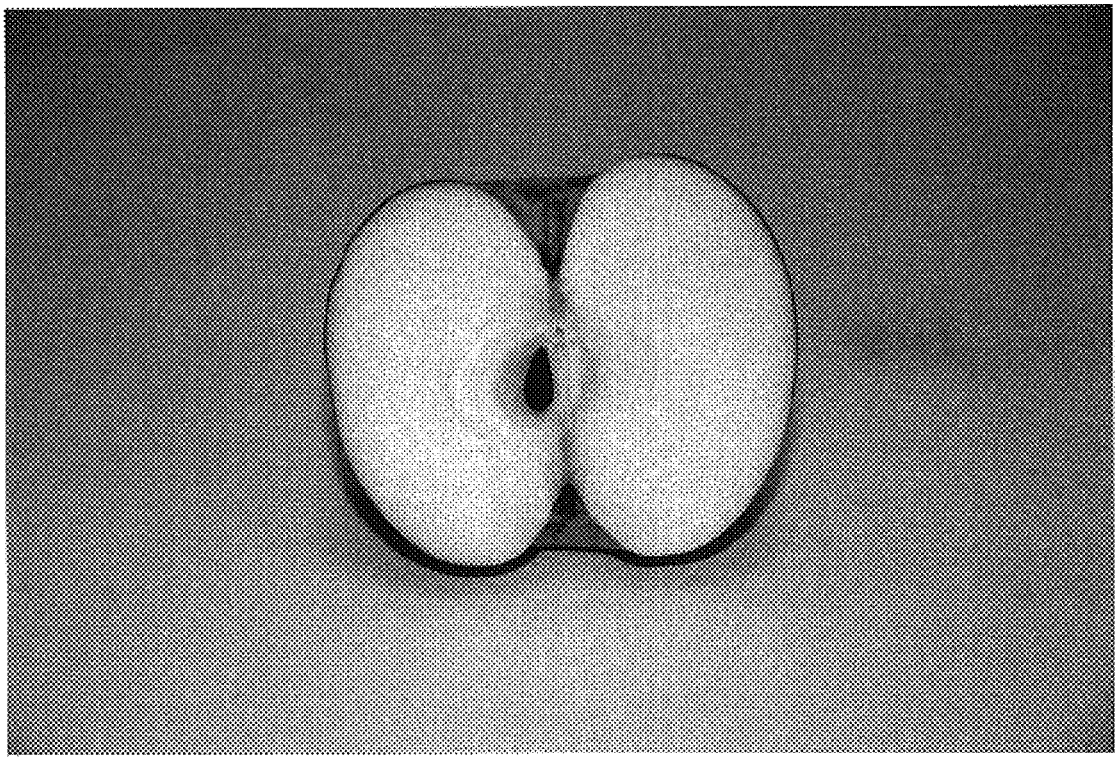
FIG. 3 shows an apple of the present variety dissected in the axial plane in order to show the flesh characteristics thereof.
Figure 4:
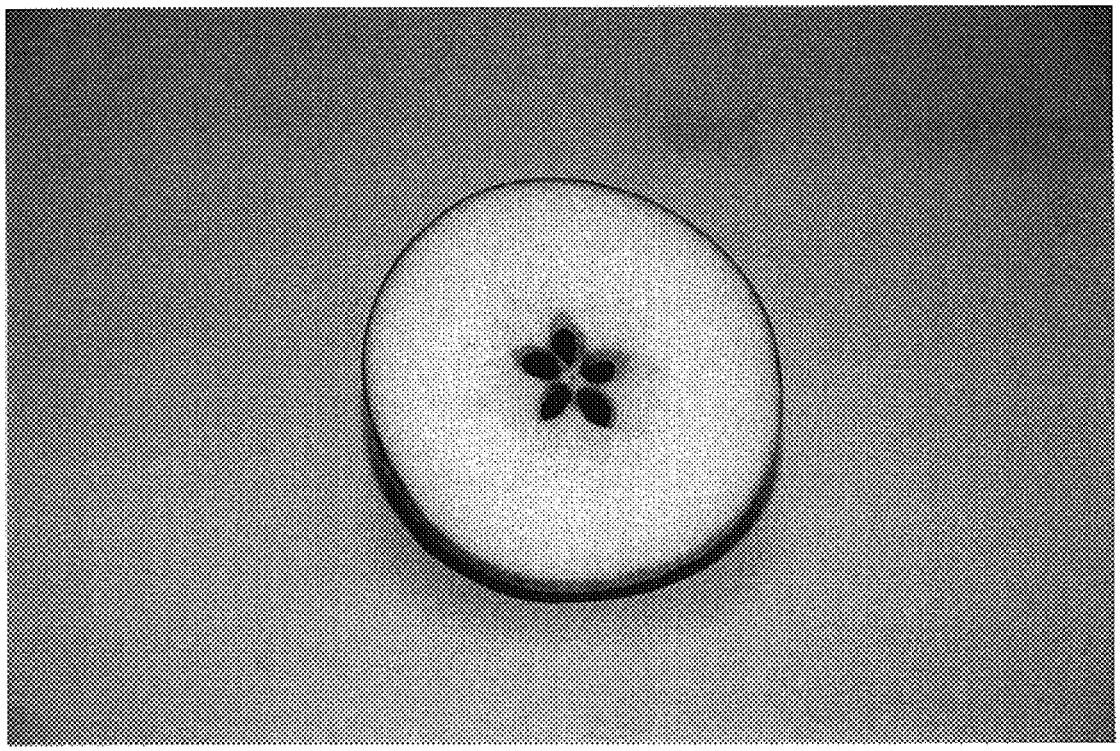
FIG. 4 is a typical fruit dissected transverse to the axial plane and showing the flesh characteristics and pips thereof.
Figure 5:
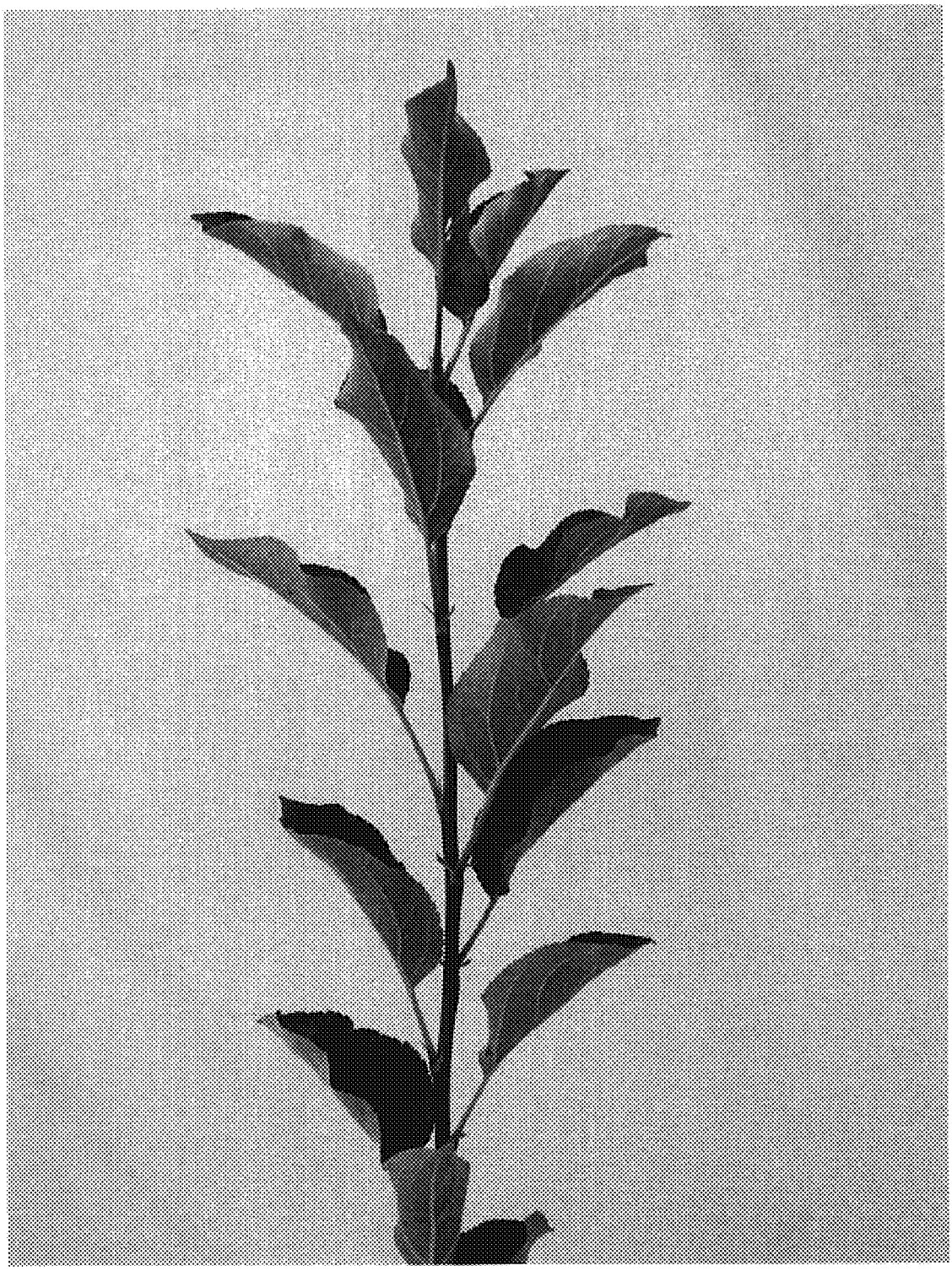
FIG. 5 depicts a typical branch and the associated foliage of the present variety.
Figure 6:
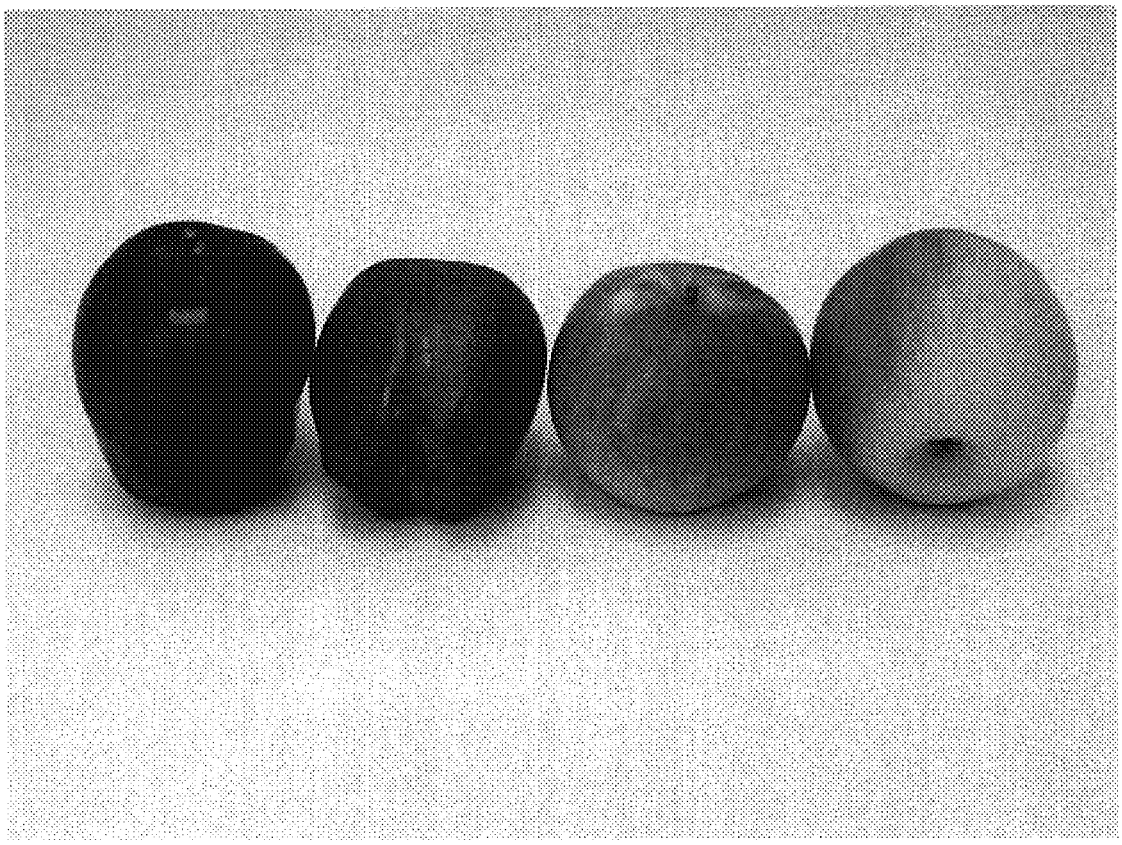
FIG. 6 depicts four fruit. The first two fruit in the photograph are fruit harvested from a 'Brisbee' Red Delicious apple trees, and which are most closely similar to the present variety in the date of harvesting. The second two fruit in the photograph are that of the present variety.

Referring more specifically to the pomological details of this new and distinct variety of apple tree, the following has been observed under the ecological conditions prevailing at the orchard of the inventor which is located in Gleed, Wash. All major color code designations by reference to the R.H.S. Colour Chart, 4$^{th}$ Edition provided by The Royal Horticulture Society of Great Britain.

Tree

*Size.*—Considered average as compared to other apple cultivars growing under the ecological conditions prevailing in Central Washington State. The original tree which is now 27 years old is about 3.5 meters in height, and about 3.5 meters in width. The second generation trees which are now 13 years old range in size from about 3.5 meters to about 4 meters in height and about 2.5 meters to about 3 meters in width.

*Productivity.*—Considered productive.

*Vigor.*—Considered moderate to vigorous.

*Density.*—Considered medium for the species.

*Regularity of bearing.*—Annual. Bearing is found on spurs and one year old shoots.

Trunk:

*Size.*—The original chance seedling tree has a circumference of 86.5 cm. when measured at a distance of about 20 cm. from the surface of the soil. The second generation trees have a size of about 33 to about 38 cm. when that measurement is taken about 20 cm. form the soil surface.

*Surface texture.*—Considered smooth to semi-rough. The roughness of the surface texture increases with advancing senecence. The surface texture is not considered distinctive of the new variety.

*Lenticels.*—Second generation trees — As a general matter, the lenticels have a length of about 1 cm. and a width of about 0.5 to about 1 cm.

*Lenticels.*—Second generation trees color — Grey-orange (RHS 167A).

Branches:

*Size.*—Average as compared to other apple cultivars growing under the ecological conditions prevailing in Central Washington State. The lower branches of the second generation trees have a diameter of about 5 cm. to 6 cm.

*Crotch angle.*—On average about 50 degrees. This characteristic is not distinctive of the present variety, however.

*Surface texture.*—Generally — Considered smooth with pronounced lenticels.

*Branching habit.*—Generally — Numerous branches are observed in young trees.

*Bark Color.*—Generally — One year old wood has a grey-green color (RHS 197B). This color appears most prominent on the base of the branch, and more redness appears toward the tips thereof (RHS 187A).

*Bud Arrangement.*—Generally — Typically the buds appear laterally on one year old wood. However, on two and three year old wood, some variability may be observed.

*Lenticels.*—Numbers — Numerous.

*Lenticels.*—Size — Small to medium for the variety.

*Lenticels.*—Color — Grey-yellow (RHS 161C).

Leaves:

*Length.*—About 95 mm.

*Width.*—About 65 mm.

*Leaf form.*—Oval to lanceolate.

*Leaf texture.*—Glabrous and glossy.

*Leaf thickness.*—Considered medium for the species.

*Leaf base.*—Shape — Considered regular.

*Leaf apex.*—Considered acuminate.

*Marginal form.*—Serrated, sharp and undulating.

*Pubescence.*—Upper surface — Weak, or completely absent.

*Pubescence.*—Lower surface — Considered weak.

*Leaf color.*—Upper surface — Mature leaves have a yellow-green coloration (RHS 147A).

*Leaf color.*—Lower surface — Mature leaves have a yellow-green coloration (RHS 148B).

*Leaf petiole.*—Shape — Considered straight.

*Leaf petiole.*—Length — About 24 mm.

*Leaf petiole.*—Diameter — About 2.2 mm.

*Leaf petiole.*—Color — Yellow-green (RHS 148C). The lower surface has a purple color. This color is not distinctive of the present variety, however.

*Leaf veins.*—Size — Considered average for the variety.

*Leaf veins.*—Position — The leaf veins lie at an angle of about 45 degrees to about 50 degrees relative to the main leaf vein.

*Leaf veins.*—Lower surface color — Yellow-green (RHS 145C).

Flowers:

*Flower buds.*—Color — Red-purple. (About RHS 59C to 61B).

*Flower buds.*—Length — About 12 mm. to about 15 mm.

*Flower buds.*—Width — About 9 mm. to about 12 mm.

*Pedicel.*—Length — About 28 mm. to about 33 mm.

*Pedicel.*—Diameter — About 1 mm.

*Pedicel.*—Color — Considered green (RHS 138A).

*Blooming time.*—Generally — The blooming time is considered to be early to mid-season in relative comparison to other apple varieties. However, the blooming time is contingent upon the geographical location and the environmental conditions prevailing at the time of bloom. As a general matter, the bloom time is similar to the Red Delicious cultivars (unpatented) growing at approximately the same geographical location in Central Washington.

*Blooming period.*—Generally — Considered medium to long for the species.

*Pollination requirements.*—The present variety appears to be currently pollinated by both 'Red Delicious' (unpatented) and 'JonaGold' apple trees (unpatented) growing in the vicinity of same. This variety therefore appears to be compatible with both diploid and triploid pollination sources.

*Number of flowers per cluster.*—As a general matter, 5 to 6 flowers appear.

*Petals.*—Numbers — 5.

*Petals.*—Length — About 19 to about 21 mm.

*Petals.*—Width — About 15 to about 17 mm.

*Petals.*—Shape — Considered ovate.

*Petals.*—Position — Considered overlapping.

*Petal margin.*—Considered straight.

*Petal texture.*—Waved.

*Petal color.*—When opened, the upper surface of the petals have a red-purple color (RHS 65A to RHS 65D). Still further, the lower surface has a reddish-purple color (RHS 62C to RHS 64D). Still further, the vein pattern in the petals has a pink color. This color does not appear distinctive of the variety, however.

*Sepals.*—Shape — Acuminate.

*Sepals.*—Marginal form — Considered straight.

*Sepals.*—Length — About 8.0 mm.

*Sepals.*—Width — About 3.0 mm.

*Sepals.*—Color — Considered green (RHS 138B) and having a red-purple tip (RHS 59A).

*Stamens.*—Numbers — About 15 are found with each flower.

*Filaments.*—Length — About 7 mm. to about 9 mm.

*Anthers.*—Shape — Considered irregular.

*Anthers.*—Length — About 2 mm.

*Anthers.*—Color — Yellow (RHS 11B).

*Pollen.*—Color — Yellow (RHS 11A).

*Pollen production.*—Generally — Considered very high.

*Pistils.*—Length — About 12 mm.

*Styles.*—Length — About 11 mm.

*Styles.*—Color — Green-yellow (RHS 1B).

*Stigma.*—Shape — Considered round to irregular.

*Stigma.*—Color — Yellow (RHS 2B).

Fruit:

*Maturity when described.*—The present variety of apple is described as it would be found at full commercial maturity, and following about 6 weeks of storage.

*Date of first picking.*—About September 29$^{th}$ under the ecological conditions prevailing in Central Washington.

*Fruit size.*—Generally — Considered medium to large for the species.

*Axial diameter.*—About 6.5 cm.

*Diameter transverse to the axial plane.*—About 7.5 cm.

*Fruit form.*—Generally — Considered uniform, round and somewhat broader in the transverse measurements. As a general matter, transverse measurements are typically about 15% greater than the axial diameter as provided, above.

*Stem cavity.*—Shape — Considered symmetrical. The stem cavity is considered acuminate at the base and the apex thereof.

*Stem cavity.*—Depth — Considered medium. About 18–22 mm.

*Stem cavity.*—Breadth — Considered average for the species. About 27 mm. to about 32 mm.

*Basin.*—Shape — Considered symmetrical and rounded.

*Basin.*—Markings — None are evident.

*Basin.*—Depth — About 13 mm.

*Basin.*—Width — About 31 mm.

*Calyx.*—Form — Slightly open and considered shallow.

*Fruit skin.*—Thickness — As a general matter, the thickness is considered medium to thin for the variety.

*Fruit skin.*—Texture — Considered smooth. No russeting is evident.

*Tendency to crack.*—Not observed.

*Skin color.*—The color of the skin has a red to pink blush (RHS 45A) with a slightly darker red stripe (RHS 46A).

*Skin color.*—Ground color — Considered yellow-green (RHS 151A) at harvest. This color softens with increasing senescence to yellow-orange (RHS 14C) following harvest.

*Flesh flavor.*—Considered distinctive with a balanced sugar to acid ratio.

*Flesh color.*—Considered creamy yellow (RHS 4D).

*Flesh texture.*—Firm and crisp.

*Soluble solids.*—Considered high, about 15.8% to 16.4%. This is, in some cases, 1.5% to about 3.3% higher than other common apple tree varieties growing under the same ecological conditions in Central Washington.

*Titratable acidity.*—About 0.851.

*Eating quality.*—Considered very good and having a sweet aromatic flavor.

*Fruit core.*—Bundle area — The fruit core with seed cells are generally considered round when viewed in the longitudinal section. The fruit core has a diameter of about 20 mm.

*Fruit bundle shape.*—Considered slightly flattened and onion shaped.

*Fruit bundle.*—Height — About 32 mm.

*Fruit bundle.*—Width — About 32 mm.

*Fruit bundle.*—Texture — Strands of conductive tissue are found in the longitudinal section.

*Calyx tube.*—Length — Considered short.
*Calyx tube.*—Form — Considered closed to slightly open.
*Calyx tube.*—Shape — Narrowly funnel shaped.
*Calyx tube.*—Depth from the calyx tube to the shoulder — About 18 mm.
*Styles.*—Generally — Present, but appear as dry residues.
*Stamens.*—Generally — Present, but appear as dry residues
*Seed cells.*—Wall thickness — Considered medium thick for the species.
*Seed cells.*—Depth — About 16 mm.
*Seed cells.*—Breadth — About 9 mm.
*Seed cells.*—Longitudinal dimension — About 18 mm. to about 20 mm.
*Seeds.*—Numbers — 6 to 10 may be found.
*Seeds.*—Numbers in one cell — 1 to 2 seeds may be found.
*Seeds.*—Length — About 9 mm. to about 11 mm.
*Seeds.*—Breadth — About 5.5 mm. to about 6.5 mm.
*Seeds.*—Form — Usually tear-dropped shaped, although slightly flattened forms may also be found.
*Seeds.*—Color — Grey-orange (RHS 166A) to brown (RHS 200B) as might be found on the tip of same.
*Stem.*—Size — Considered short, stout and slightly pubescent.
*Stem.*—Length — About 7 mm.
*Stem.*—Width — About 2.4 mm.
*Eating quality.*—Considered good to excellent.

Although the new variety of apple tree herein denominated as 'Emmons' possesses the described characteristics when grown under the ecological conditions prevailing in the Columbia Basin of Central Washington, it is to be understood that variations of the usual magnitude and characteristics incident to changes in growing conditions, fertilization, pruning and pest control are to be expected.

Having thus described and illustrated my new variety of apple tree, what I claim is new, and desire to secure by Plant Letters Patent is:

1. A new and distinct variety of apple tree as substantially illustrated and described and which is mature for harvesting and shipment about September 29$^{th}$ when grown under the ecological conditions prevailing in the Columbia Basin of Central Washington.

* * * * *